United States Patent
Long et al.

(10) Patent No.: US 11,547,611 B2
(45) Date of Patent: Jan. 10, 2023

(54) WOUND DRESSINGS AND SYSTEMS WITH HIGH-FLOW THERAPEUTIC GAS SOURCES FOR TOPICAL WOUND THERAPY AND RELATED METHODS

(71) Applicant: KCI LICENSING, INC., San Antonio, TX (US)

(72) Inventors: Justin Alexander Long, Wimborne (GB); Christopher Brian Locke, Bournemouth (GB)

(73) Assignee: KCI LICENSING, INC., San Antonio, TX (US)

(*) Notice: Subject to any disclaimer, the term of this patent is extended or adjusted under 35 U.S.C. 154(b) by 193 days.

(21) Appl. No.: 16/648,507

(22) PCT Filed: Sep. 21, 2018

(86) PCT No.: PCT/US2018/052137
§ 371 (c)(1),
(2) Date: Mar. 18, 2020

(87) PCT Pub. No.: WO2019/060667
PCT Pub. Date: Mar. 28, 2019

(65) Prior Publication Data
US 2020/0214897 A1 Jul. 9, 2020

Related U.S. Application Data

(60) Provisional application No. 62/561,740, filed on Sep. 22, 2017.

(51) Int. Cl.
*A61F 13/00* (2006.01)
*A61F 13/02* (2006.01)
*A61M 1/00* (2006.01)

(52) U.S. Cl.
CPC .. *A61F 13/00046* (2013.01); *A61F 13/00068* (2013.01); *A61F 13/0209* (2013.01);
(Continued)

(58) Field of Classification Search
CPC .......... A61F 13/00046; A61F 13/00068; A61F 13/0209; A61F 2013/0017; A61F 2013/00255; A61M 1/90
See application file for complete search history.

(56) References Cited

U.S. PATENT DOCUMENTS

2002/0065494 A1* 5/2002 Lockwood .............. A61M 1/90
604/327
2003/0050674 A1 3/2003 Joshi
(Continued)

FOREIGN PATENT DOCUMENTS

CN 205924317 2/2017
EP 2628500 A1 * 8/2013 ....... A61F 13/00068
(Continued)

OTHER PUBLICATIONS

International Search Report and Written Opinion issued in Corresponding PCT Application No. PCT/US2018/052137, dated Dec. 19, 2018.
(Continued)

*Primary Examiner* — Susan S Su
*Assistant Examiner* — Eric Rassavong

(57) ABSTRACT

This disclosure includes wound dressings and systems with high-flow therapeutic gas sources for topical wound therapy and related methods. Some dressings, which are configured to be coupled to tissue to facilitate delivery of therapeutic gas to the tissue, comprise a manifold that defines a plurality of gas passageways, the manifold configured to allow communication of therapeutic gas to the tissue; and a gas-occlusive layer configured to be disposed over the manifold
(Continued)

and coupled to the tissue such that an interior volume containing the manifold is defined between the gas-occlusive layer and the tissue and the gas-occlusive layer limits escape of therapeutic gas from the interior volume; wherein the gas-occlusive layer includes: a first opening configured to allow communication of therapeutic gas into the interior volume; and one or more second openings configured to allow communication of therapeutic gas out of the interior volume.

12 Claims, 7 Drawing Sheets

(52) U.S. Cl.
CPC ....... *A61M 1/90* (2021.05); *A61F 2013/0017* (2013.01); *A61F 2013/00255* (2013.01)

(56) References Cited

U.S. PATENT DOCUMENTS

| | | | |
|---|---|---|---|
| 2004/0260253 A1 | 12/2004 | Rosati | |
| 2006/0200100 A1 | 9/2006 | Rosati | |
| 2009/0227969 A1 | 9/2009 | Jaeb et al. | |
| 2009/0259171 A1* | 10/2009 | Joshi | A61K 9/0021 604/23 |
| 2010/0069858 A1 | 3/2010 | Olson | |
| 2010/0262095 A1* | 10/2010 | Hall | A61M 1/86 604/319 |
| 2010/0305490 A1* | 12/2010 | Coulthard | A61M 1/962 604/313 |
| 2011/0282309 A1* | 11/2011 | Adie | A61M 1/90 604/319 |
| 2012/0059301 A1 | 3/2012 | Franklin | |
| 2012/0209226 A1 | 8/2012 | Simmons et al. | |
| 2013/0317406 A1* | 11/2013 | Locke | A61M 1/784 604/358 |
| 2014/0107562 A1* | 4/2014 | Dorian | A61M 1/90 604/23 |
| 2015/0374552 A1* | 12/2015 | Lee | A61F 13/00046 602/47 |
| 2016/0030722 A1 | 2/2016 | Anderson et al. | |
| 2016/0166781 A1* | 6/2016 | Sarangapani | A61M 1/0023 604/23 |
| 2016/0175500 A1 | 6/2016 | Cali et al. | |
| 2017/0014273 A1* | 1/2017 | Woodroof | A61L 27/56 |
| 2017/0189237 A1* | 7/2017 | Locke | A61F 13/0256 |
| 2017/0209311 A1* | 7/2017 | Kanchagar | B32B 27/12 |
| 2017/0319394 A1 | 11/2017 | Chen et al. | |

FOREIGN PATENT DOCUMENTS

| | | | |
|---|---|---|---|
| EP | 2956101 | 12/2015 | |
| GB | 2333724 A * | 1/1998 | ....... A61F 13/00046 |
| TW | 200942281 | 10/2009 | |
| TW | M525742 | 7/2016 | |
| WO | WO 1996/032082 | 10/1996 | |
| WO | WO 2009/066106 | 5/2009 | |
| WO | WO-2009066105 A1 * | 5/2009 | ....... A61F 13/00063 |
| WO | WO 2009/097534 | 8/2009 | |
| WO | WO 2009/146441 | 12/2009 | |
| WO | WO 2009/158500 | 12/2009 | |
| WO | WO 2011/008497 | 1/2011 | |
| WO | WO 2011/008711 | 1/2011 | |
| WO | WO 2013/066694 | 5/2013 | |
| WO | WO 2014/144762 | 9/2014 | |
| WO | WO 2015/123353 | 8/2015 | |

OTHER PUBLICATIONS

International Search Report and Written Opinion issued in Corresponding PCT Application No. PCT/US2018/051408, dated Jan. 23, 2019.

International Search Report and Written Opinion issued in Corresponding PCT Application No. PCT/US2019/012250, dated May 7, 2019.

International Search Report and Written Opinion issued in Corresponding PCT Application No. PCT/US2019/012273, dated May 16, 2019.

International Search Report and Written Opinion Issued in Corresponding PCT Patent Application No. PCT/US2018/057214, dated Jan. 31, 2019.

* cited by examiner

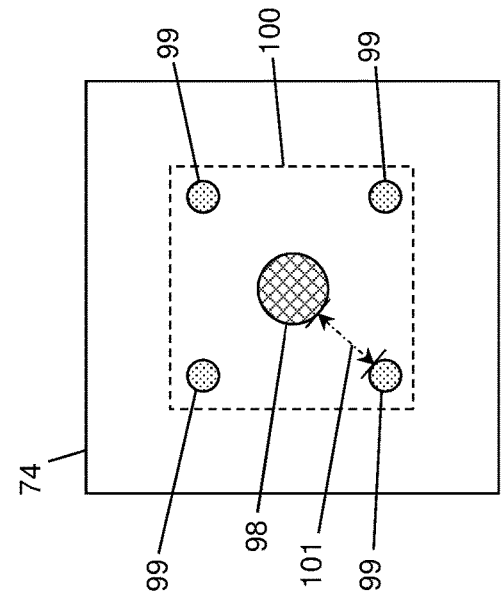
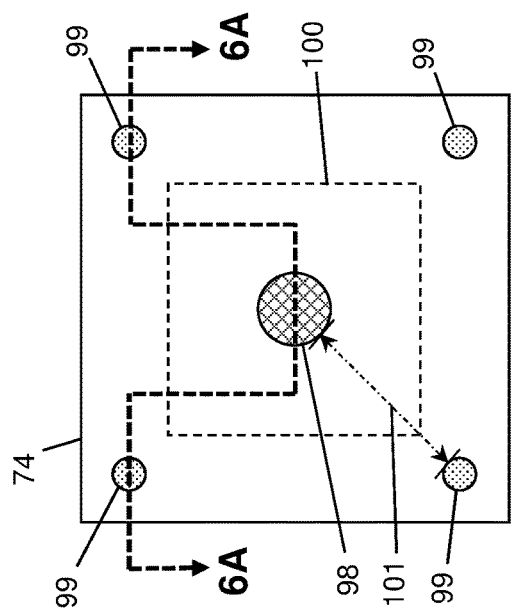
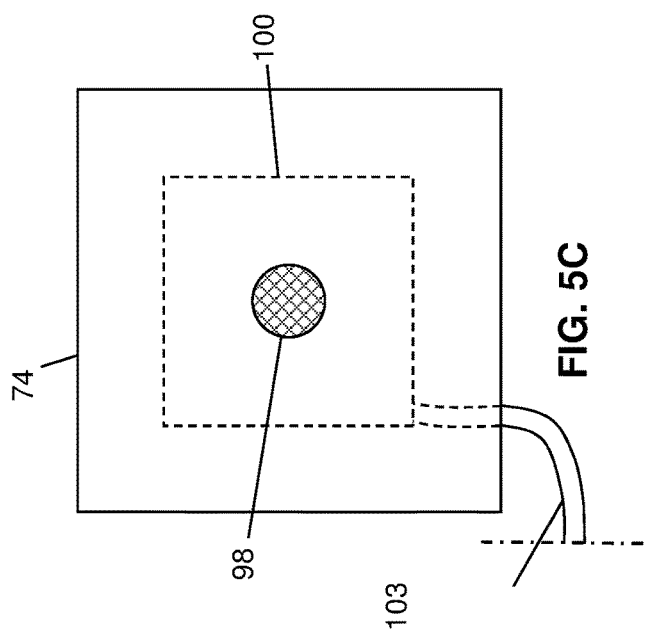

WOUND DRESSINGS AND SYSTEMS WITH HIGH-FLOW THERAPEUTIC GAS SOURCES FOR TOPICAL WOUND THERAPY AND RELATED METHODS

CROSS-REFERENCE TO RELATED APPLICATIONS

This application is a national phase application under 35 U.S.C. § 371 of International Application No. PCT/US2018/052137, filed Sep. 21, 2018, which claims the benefit of U.S. Provisional Application No. 62/561,740, filed Sep. 22, 2017, the contents of which applications are incorporated herein in their entirety.

BACKGROUND

1. Field of Invention

The present invention relates generally to wound dressings, and more specifically, but not by way of limitation, to wound dressings and systems with high-flow therapeutic gas sources for topical wound therapy and related methods.

2. Description of Related Art

Clinical studies and practice have shown that topical applications of therapeutic gas can reduce tissue inflammation and/or improve tissue proliferation (e.g., improve collagen synthesis, growth factor production, angiogenesis, and/or the like).

Traditional oxygen-based therapies supply oxygen at relatively low-flow rates, such as, for example, between 3 and 13 milliliters per hour. Although these traditional oxygen-based therapies can supply high-purity oxygen (e.g., via electrolysis of atmospheric water vapor) to wound dressings, these therapies may require multiple hours or even days of operation before the oxygen concentration at the target tissue is double that of the oxygen concentration in ambient air (e.g., approximately 20.95 percent oxygen concentration).

Thus, while the clinical benefits of topical applications of therapeutic gas, and in particular, therapeutic oxygen, are known, improvement to the efficacy, convenience, and/or simplicity of therapy systems, components, and related methods may benefit healthcare providers and patients.

SUMMARY

One or more embodiments of the present devices, systems, and/or methods can provide greater efficacy and/or accuracy in the supply and/or delivery of the topical application of therapeutic gas, such as, for example, oxygen, to target tissue.

Some embodiments of the present dressings comprise a manifold that defines a plurality of gas passageways, the manifold configured to allow communication of therapeutic gas to the tissue; and a gas-occlusive layer configured to be disposed over the manifold and coupled to the tissue such that an interior volume containing the manifold is defined between the gas-occlusive layer and the tissue and the gas-occlusive layer limits escape of therapeutic gas from the interior volume; wherein the gas-occlusive layer includes: a first opening configured to allow communication of therapeutic gas into the interior volume; and one or more second openings configured to allow communication of therapeutic gas out of the interior volume.

In some embodiments, each of the one or more second openings includes a transverse dimension of approximately 1 to 10 millimeters (mm). In some embodiments, for each of the one or more second openings, a distance between the second opening and the first opening is approximately equal to a distance between each other of the second openings and the first opening.

In some embodiments, the gas-occlusive layer comprises one or more filters configured to allow communication of therapeutic gas out of the interior volume through the one or more second openings and restrict communication of exudate out of the interior volume through the one or more second openings. In some embodiments, the one or more filters are bonded to an upper surface or a lower surface of the gas-occlusive layer. In some embodiments, at least one of the one or more filters includes a pore size of approximately 0.05 to 0.15 micrometers. In some embodiments, the pore size is approximately 0.1 micrometers. In some embodiments, at least one of the one or more filters includes a non-woven textile. In some embodiments, at least one of the one or more filters includes polytetrafluoroethylene or polyolefin.

Some embodiments of the present dressings comprise a liquid control layer having a plurality of perforations, the liquid control layer configured to be disposed between the manifold and the tissue to restrict communication of exudate toward the tissue. In some embodiments, the liquid control layer comprises a foam or a non-woven textile. In some embodiments, the liquid control layer comprises a hydrophilic material, optionally, a superabsorbent polymer. In some embodiments, the liquid control layer comprises a film. In some embodiments, the liquid control layer includes an opening and at least a portion of the first opening of the gas-occlusive layer overlies at least a portion of the opening of the liquid control layer.

In some embodiments, the manifold includes an opening and at least a portion of the first opening of the gas-occlusive layer overlies at least a portion of the opening of the manifold. In some embodiments, the manifold comprises polyethylene, a polyolefin, or a co-polyester. In some embodiments, the manifold comprises a foam or a non-woven textile.

Some embodiments of the present dressings comprise a port configured to extend through the first opening of the gas-occlusive layer to guide the communication of therapeutic gas into the interior volume. In some embodiments, the port is configured to extend through the opening of the manifold and the opening of the liquid control layer to guide the communication of therapeutic gas into the interior volume.

Some embodiments of the present dressings comprise a patient-interface layer configured to be disposed below the liquid control layer and in contact with the tissue, the patient-interface layer defining a plurality of openings configured to allow communication of therapeutic gas and exudate through the patient-interface layer. In some embodiments, the patient-interface layer comprises silicone, polyethylene, or ethylene vinyl acetate. In some embodiments, the patient-interface layer includes an adhesive configured to couple the patient-interface layer to the tissue.

Some embodiments of the present dressings comprise a sorbent material configured to be disposed above or below the manifold and to capture exudate. In some embodiments, the dressing comprises a sorbent layer that includes the sorbent material. In some embodiments, the sorbent layer has a plurality of perforations; the sorbent layer has a plurality of openings; and/or a planform area of the sorbent layer is smaller than a planform area of the manifold. In some embodiments, the sorbent layer comprises a foam or a non-woven textile. In some embodiments, the sorbent material comprises a superabsorbent polymer. In some embodiments, the sorbent material comprises a carbon filter configured to facilitate the filtration of therapeutic gas within the interior volume.

Some embodiments of the present systems comprise one of the present dressings and a therapeutic gas source in fluid communication with the dressing, wherein the therapeutic gas source is configured to provide therapeutic gas to the interior volume of the dressing at a flow rate of at least approximately 100 cubic centimeters per minute.

In some embodiments, the flow rate of the therapeutic gas is at least approximately 500 cubic centimeters per minute. In some embodiments, the flow rate of the therapeutic gas is approximately two liters per minute. In some embodiments, the therapeutic gas includes oxygen. In some embodiments, the oxygen has an oxygen concentration of at least 90 percent. In some embodiments, the oxygen source comprises an oxygen concentrator. In some embodiments, the oxygen concentrator is configured to provide a pulsatile flow of oxygen.

Some embodiments of the present systems include a negative pressure source; and a valve movable between a first position wherein fluid communication is permitted between the therapeutic gas source and the dressing and a second position wherein fluid communication is permitted between the therapeutic gas source and the negative pressure source. In some embodiments, the valve includes a solenoid valve.

Some embodiments of the present systems include a conduit configured to provide fluid communication between the dressing and the therapeutic gas source.

Some embodiments of the present methods comprise coupling one of the present dressings to a patient's tissue; and communicating therapeutic gas from a therapeutic gas source into the interior volume of the dressing, wherein the therapeutic gas is communicated at a flow rate of at least approximately 100 cubic centimeters per minute.

In some embodiments, the flow rate at which the therapeutic gas is communicated into the interior volume is at least approximately 500 cubic centimeters per minute. In some embodiments, the flow rate at which the therapeutic gas is communicated into the interior volume is approximately two liters per minute. In some embodiments, the therapeutic gas includes oxygen. In some embodiments, the oxygen has an oxygen concentration of at least 90 percent.

Some embodiments of the present methods comprise communicating therapeutic gas from the therapeutic gas source to a negative pressure source. In some embodiments, when communicating the therapeutic gas between the therapeutic gas source and the negative pressure source, communication of the therapeutic gas between the therapeutic gas source and the interior volume of the dressing is restricted. In some embodiments, the communication of the therapeutic gas between the therapeutic gas source and the negative pressure source is performed for a time duration of approximately five to seven seconds. In some embodiments, after the time duration, the method includes communicating the therapeutic gas between the therapeutic gas source and the interior volume of the dressing. In some embodiments, after the time duration, when communicating the therapeutic gas between the therapeutic gas source and the interior volume of the dressing, communication of the therapeutic gas between the therapeutic gas source and the negative pressure source is restricted. In some embodiments, communication of the therapeutic gas from the therapeutic gas source is alternated between the negative pressure source and the interior volume of the dressing once approximately every 10 seconds.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or. The phrase "and/or" includes any and all combinations of one or more of the associated listed items. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, an apparatus that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures. Figures having schematic views are not drawn to scale.

FIGS. 5A-5C are top views of structures for controlling a positive pressure within some embodiments of the present dressings.

DETAILED DESCRIPTION

Figure 1:
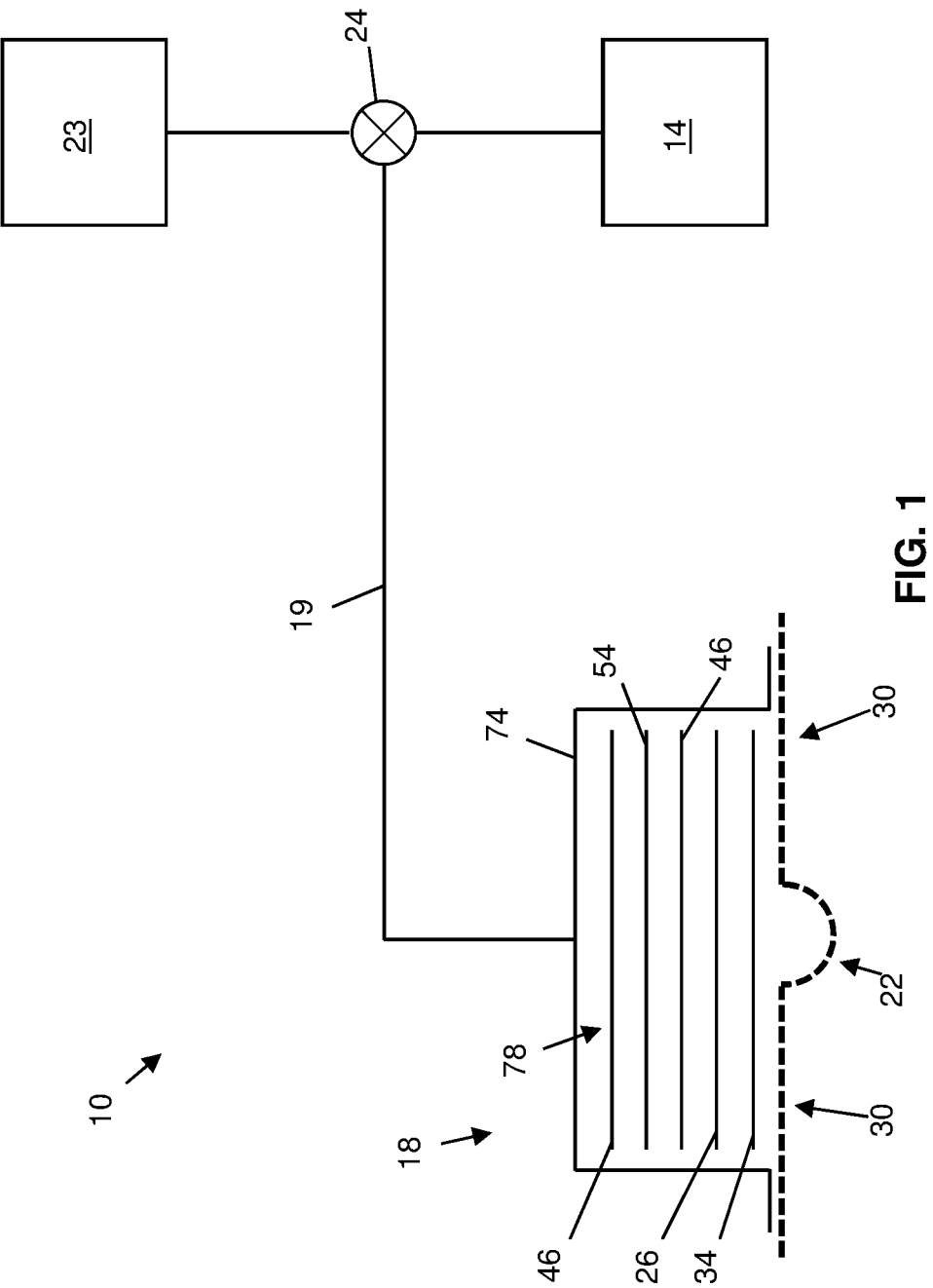
FIG. 1 is a schematic view of a first embodiment of the present systems.

Referring to FIG. 1, shown therein and designated by the reference numeral 10 is one embodiment of the present systems for providing topical wound therapy. System 10 includes a therapeutic gas source 14 and a wound dressing 18 configured to be coupled to target tissue 22 and/or to tissue 30 surrounding the target tissue to facilitate delivery of therapeutic gas to the target tissue.

The term "target tissue" as used herein can broadly refer to a wound, a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The term "target tissue" as used herein can also refer to areas of tissue that are not necessarily wounded or exhibit a disorder, but include tissue that would benefit from tissue generation. The term "wound" as used herein can refer to a chronic, subacute, acute, traumatic, and/or dehisced incision, laceration, puncture, avulsion, and/or the like, a partial-thickness and/or full thickness burn, an ulcer (e.g., a diabetic, pressure, venous, and/or the like), flap, and/or graft.

Therapeutic gas source 14 can be configured to be in fluid communication with dressing 18 via a conduit 19. Therapeutic gas source 14 can be configured to provide therapeutic gas to an interior volume (e.g., 78) defined by dressing 18 (as described in further detail below).

Therapeutic gas source 14 can comprise any suitable device configured to supply therapeutic gas to dressing 18 at a volumetric flow rate of at least approximately 100 cubic centimeters per minute (cm$^3$/min), such as, for example, 200, 300, 400, 500, 600, 700, 800, 900, 1000, 1500, 2000, 2500, 3000 cm$^3$/min or more. Therapeutic gas source 14 can be configured to supply any gas suitable for treating target tissue 22, such as, for example, oxygen. More particularly, therapeutic gas supplied by therapeutic gas source 14 can comprise an oxygen concentration of at least 80 percent, such as, for example, 80, 85, 90, 92, 94, 96, 98 or more percent. By providing therapeutic gas to dressing 18 at one or more of the volumetric flow rates and/or oxygen concentrations described herein, system 10 can attain a steady-state oxygen concentration of at least 80 percent (e.g., 80, 85, 90, 92, 94, 96, 98 or more percent) within an interior volume (e.g., 78) of the dressing within a time duration of approximately 2 to 10 minutes (e.g., approximately any one of, or between approximately any two of: 2, 3, 4, 5, 6, 7, 8, 9 and 10 minutes). To illustrate, by increasing the volumetric flow rate of therapeutic gas into dressing 18, the duration of time needed to reach a steady-state oxygen concentration of at least 80 percent decreases, and vice versa.

Therapeutic gas source 14 may comprise any suitable device configured to supply therapeutic gas to dressing 18 at one or more of the volumetric flow rates and/or oxygen concentrations described herein, such as, for example, an oxygen concentrator, a liquid oxygen reservoir, a reservoir having compressed oxygen gas, and/or the like.

Therapeutic gas source 14 can be configured to provide a pulsatile or continuous flow of therapeutic gas to dressing 18. For example, in embodiments where therapeutic gas source 14 comprises a conventional pulsatile oxygen concentrator, the therapeutic gas source can comprise one or more sensors configured to detect data indicative of negative pressure (e.g., caused by a patient's inhalation), which may be required to begin and/or to continue the pulsed doses of therapeutic gas from the therapeutic gas source. As used herein, "negative pressure" can refer to a pressure that is less than a local ambient pressure, such as less than atmospheric pressure. As a safety measure in such conventional pulsatile oxygen concentrators, an absence of a detection of data indicative of negative pressure (e.g., caused by a patient's inhalation) within a predetermined duration of time (e.g., within 2, 4, 6, 8, 10, 12, 14, or 15 minutes) may cause the therapeutic gas source to stop supplying therapeutic gas.

Because system 10 may not be configured to receive such a negative pressure via inhalation from a patient, the system can comprise a negative pressure source 23 configured to be in fluid communication with therapeutic gas source 14 to provide such a negative pressure, which may simulate inhalation from a patient. Negative pressure source 23 may be configured to apply a relative low negative pressure, such as, for example, approximately 2, 4, 6, 8, or 10 millimeters of mercury (mmHg). Negative pressure source 23 can comprise a reservoir of gas held within the reservoir at a negative pressure, the gas being in selective communication with therapeutic gas source 14 to provide negative pressure. Negative pressure source 23 can comprise a mechanically and/or electrically-powered device, such as, for example, a vacuum pump, a suction pump, a wall suction port, a micro-pump, and/or the like that can provide negative pressure to therapeutic gas source 14.

System 10 includes a valve 24 configured to control fluid flow between therapeutic gas source 14, dressing 18, and negative pressure source 23. More particularly, valve 24 can be movable between a first position wherein fluid communication is permitted between therapeutic gas source 14 and an interior volume (e.g., 78) of dressing 18 and a second position wherein fluid communication is permitted between the therapeutic gas source and negative pressure source 23. When valve 24 is in the first position, communication of therapeutic gas between therapeutic gas source 14 and negative pressure source 23 is restricted. Conversely, when valve 24 is in the second position, communication of therapeutic gas between therapeutic gas source 14 and dressing 18 is restricted.

Valve 24 can be configured to remain in the second position for any suitable duration of time, such as, for example, approximately 2, 3, 4, 5, 6, 7, or more seconds, such that one or more sensors of therapeutic gas source 14 detect data indicative of a negative pressure sufficient to begin and/or continue the supply of therapeutic gas from the therapeutic gas source. Valve 24 can be configured to alternate between the first and second position at any suitable frequency, such as, for example, once every 2, 4, 6, 8, 10, 12, 14, or 15 minutes. Valve 24 can comprise any valve suitable to control fluid flow between therapeutic gas source 14, dressing 18, and negative pressure source 23, such as, for example, a solenoid valve. Valve 24 may be mechanically and/or electrically-actuated.

Figure 2:
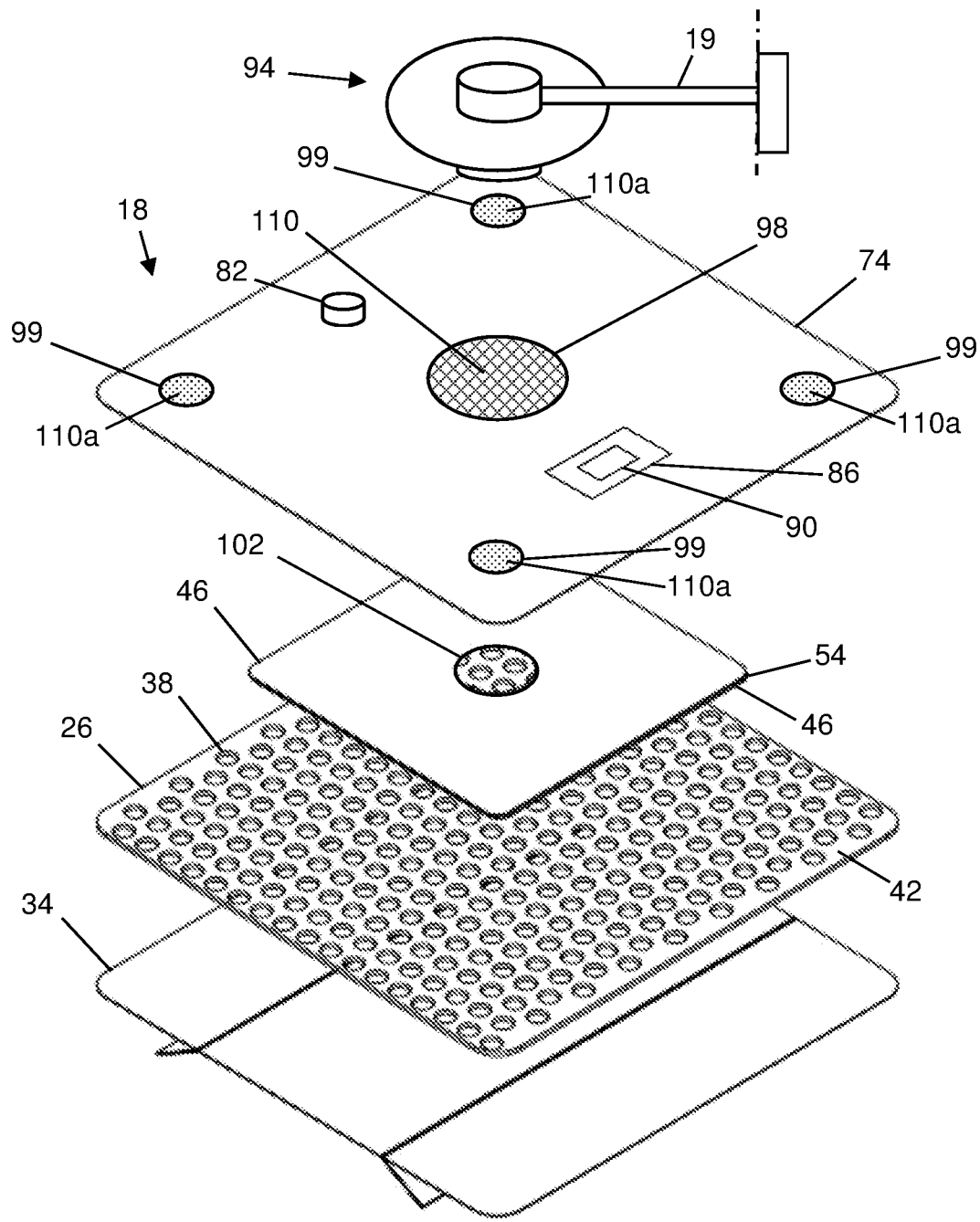
FIG. 2 is an exploded perspective view of a first embodiment of the present wound dressings, suitable for use in some embodiments of the present systems.

Referring now to FIGS. 1 and 2, dressing 18 can include a patient-interface layer 26 configured to be in contact with target tissue 22 and/or tissue 30 surrounding the target tissue. For example, patient-interface layer 26 may be disposed over target tissue 22 and be in contact with tissue 30 surrounding the target tissue. For further example, patient-interface layer 26 may be disposed over target tissue 22 such that the patient-interface layer fills at least a portion of a recess defined by the target tissue. Patient-interface layer 26 can comprise any suitable planform shape, planform area, thickness, and/or the like that is appropriate to treat target tissue 22.

Patient-interface layer 26 can comprise an adhesive configured to couple the patient-interface layer to target tissue 22 and/or tissue 30 surrounding the target tissue. Such an adhesive can be configured to have low tack properties to minimize patient discomfort and/or tissue trauma as a result of the application, repositioning, and/or removal of patient-interface layer 26 from target tissue 22 and/or tissue 30 surrounding the target tissue. Such an adhesive may comprise any suitable adhesive, such as, for example, an acrylic adhesive, polyurethane gel adhesive, silicone adhesive, hydrogel adhesive, hydrocolloid adhesive, a combination thereof, and/or the like. Dressing 18 may include a protective liner 34 configured to be disposed on a surface of patient-interface layer 26 such that the protective liner at least partially covers the adhesive (e.g., prior to application of the dressing onto tissue).

Patient-interface layer 26 can comprise a plurality of openings 38 configured to allow communication of therapeutic gas and exudate through the patient-interface layer and/or to promote granulation of target tissue 22. As shown, each of openings 38 of patient-interface layer 26 includes a circular shape. Openings 38 of patient-interface layer 26 can comprise any suitable shape, such as, for example, circular, elliptical, or otherwise round, square, rectangular, hexagonal, or otherwise polygonal. Each of openings 38 of patient-interface layer 26 may be substantially equal in size (e.g., as measured by a maximum transverse dimension of the opening), such as, for example, approximately any one of, or between approximately any two of, the following: 0.5, 0.75, 1.0, 1.25, and 1.5 centimeters (cm). In some embodiments, a patient-interface layer (e.g., 26) may comprise openings (e.g., 38) having different sizes.

Patient-interface layer 26 can comprise a plurality of gas passageways 42 defined by any suitable material, such as, for example, an open-cell foam (e.g., reticulated foam). Each gas passageway 42 can comprise a maximum transverse dimension of 400 and 600 micrometers. Patient-interface layer 26 can be hydrophilic. For example, patient-interface layer 26 can be configured to wick away (e.g., by capillary flow through gas passageways 42) exudate from target tissue 22 and/or tissue 30 surrounding the target tissue.

Patient-interface layer 26 can comprise any suitable material, such as, for example, a polymer, optionally, silicone, a hydrogel, polyvinyl alcohol, polyethylene, a polyurethane, polyether, ethylene vinyl acetate, a copolymer thereof, or a blend thereof. In some embodiments, a patient-interface layer (e.g., 26) can serve as or include a scaffold to promote tissue generation. Such a scaffold may include calcium phosphate, a hydroxyapatite (e.g., coralline hydroxyapatite), a carbonate (e.g., calcium carbonate), allograft tissue, autograft tissue, collagen, polylactic acid (PLA), polyglycolic acid (PGA), and/or the like. In some embodiments, a patient-interface layer (e.g., 26) may comprise a biodegradable material, such as, for example, PLA, PGA, a polycarbonate, polypropylene fumarate, polycaprolactone, a polymeric blend thereof, and/or the like.

Non-limiting examples of patient-interface layer 26 include Silbione® HC2 products, which are commercially available from Bluestar Silicones International, of Lyon, France, and Nanova™ absorptive dressings, which are commercially available from Kinetic Concepts Inc., of San Antonio, Tex., USA.

Dressing 18 can include one or more manifolds 46. Each manifold 46 can be configured to allow communication of therapeutic gas to target tissue 22 and/or allow communication of exudate to a sorbent material (e.g., 58) (discussed in further detail below). For example, each manifold 46 can define a plurality of gas passageways 50 to distribute therapeutic gas across the manifold and/or to collect exudate from target tissue 22 across the manifold. Plurality of gas passageways 50 of each manifold 46 can be interconnected to improve distribution and/or collection of fluids across the manifold. For example, gas passageways 50 can be defined by an open-cell foam (e.g., reticulated foam), tissue paper, gauze, a non-woven textile (e.g., felt), and/or the like. Manifold 46 can comprise any suitable material, such as, for example, polyethylene, a polyolefin, a polyether, polyurethane, a co-polyester, a copolymer thereof, or a blend thereof. Manifold 46 can comprise any suitable planform shape, planform area, thickness, and/or the like that is appropriate to treat target tissue 22.

Non-limiting examples of manifold 46 include Medisponge® Foams, which are commercially available from Essentra PLC of Milton Keynes, England, and Exudate Management Systems, which are commercially available from TWE Group GmbH, of Emsdetten, Germany.

Figure 6A:
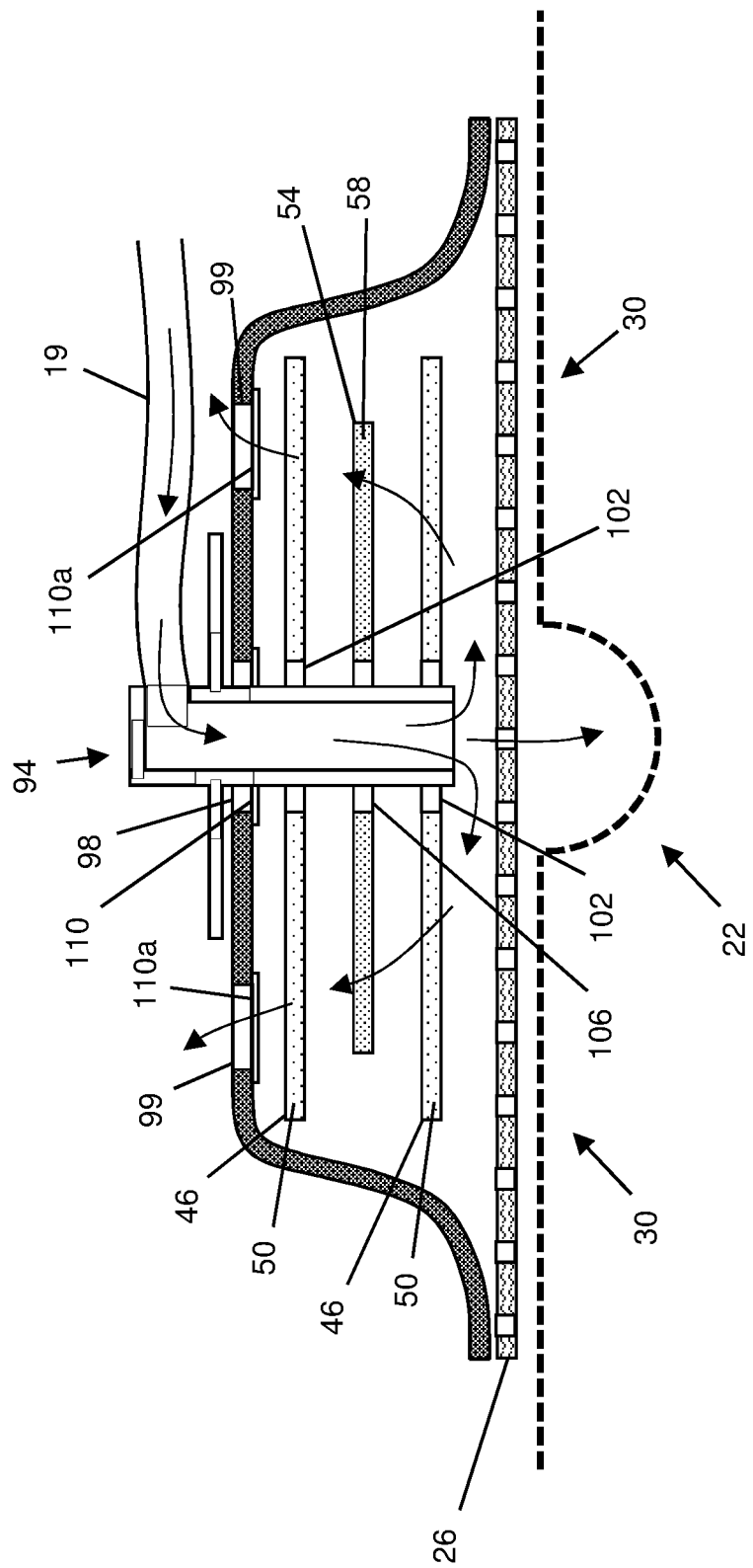
FIG. 6A is a cross-sectional side view of the dressing of FIG. 2, taken along line 6A-6A of FIG. 5A, shown with a port extending through a portion thereof.
Figure 6B:
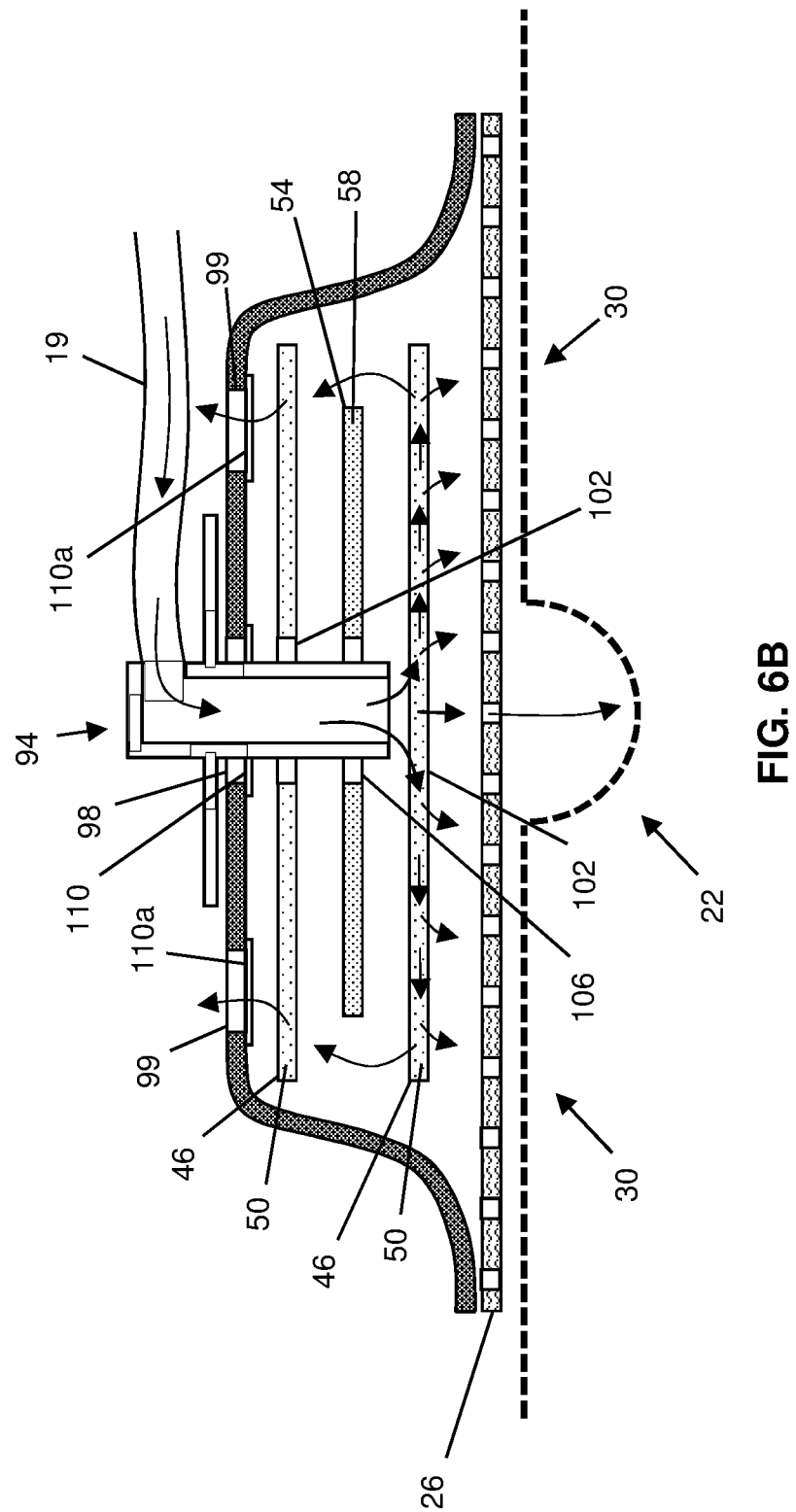
FIG. 6B is a second cross-sectional side view of the dressing of FIG. 2, taken along line 6A-6A of FIG. 5A, shown with a port extending through a portion thereof.

Dressing 18 can include a sorbent layer 54. Sorbent layer 54 can include a sorbent material 58 configured to capture exudate. Sorbent material 58 can be disposed below or above one of manifolds 46. As shown in FIGS. 2, 6A, and 6B, sorbent material 58 can be disposed between a first one of manifolds 46 and a second one of the manifolds. Sorbent layer 54, and, more particularly, sorbent material 58, can comprise any suitable adsorbent or absorbent material. Suitable examples of an absorbent material (e.g., a material that tends to swell, by 50 percent or more, due to the binding of liquid within the material) includes a foam, a non-woven textile, a superabsorbent polymer, and/or the like. For example, sorbent material 58 having absorbent material may comprise sodium carboxymethyl cellulose (NaCMC) fiber, alginate fiber, and/or the like. Suitable examples of an adsorbent material (e.g., a material that has a surface onto which liquid binds such that the material does not swell) include carbon filters, such as, for example, an activated charcoal filter and/or the like. Such an activated charcoal filter can be configured to remove nitrogen from therapeutic gas supplied from therapeutic gas source 14 into dressing 18. In this way and others, sorbent material 58 can facilitate the filtration of nitrogen within interior volume 78 of dressing 18.

Non-limiting examples of sorbent material 58 include superabsorbent wound care laminates having a density of 300 grams per square meter (GSM), which are commercially available from Gelok International of Dunbridge, Ohio, USA, and Absorflex™, which has a density of 800 GSM and is commercially available from Texsus S.p.A. of Chiesina Uzzanese, Italy.

Figure 3:
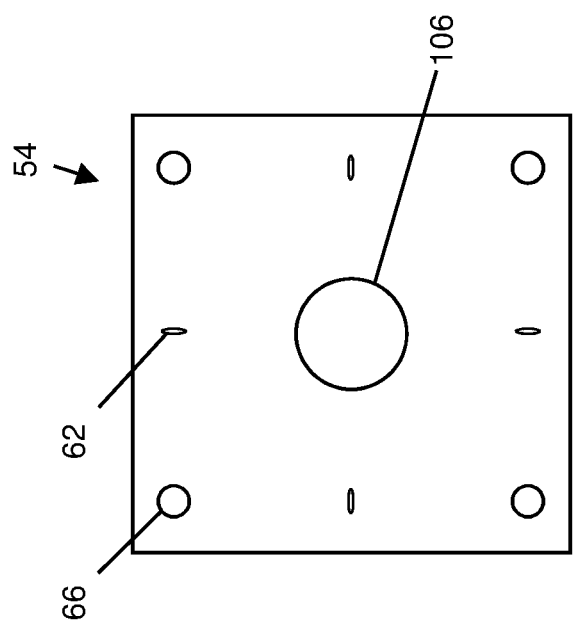
FIG. 3 is a top view of an embodiment of a sorbent layer, suitable for use in some embodiments of the present systems.

As shown in FIG. 3, sorbent layer 54 can comprise a plurality of perforations 62 and/or a plurality of openings 66, one or more of which are configured to allow fluid communication through the sorbent layer in instances where sorbent material 58 exhibits gel-blocking. Gel-blocking can occur when sorbent material 58 forms a gel in response to absorption of liquid. Gel-blocking can cause sorbent material 58 to block liquid and/or gas flow through the sorbent material. In some embodiments, sorbent layer 54 can comprise a textured surface configured to distribute liquid into and/or around sorbent material 58.

In this embodiment, each opening 66 may define an aperture comprising a perimeter that does not substantially change (e.g., does not change by more than 5%) in response to fluid flow through the opening. Each perforation 62 may define an aperture comprising a perimeter that substantially changes (e.g., changes by more than 5%) in response to fluid flow through the perforation. For example, one or more of perforations 62 may be defined by a slit in sorbent layer 54. Each of openings 66 of sorbent layer 54 may be substantially equal in size (e.g., as measured by a maximum transverse dimension of the opening), such as, for example, approximately any one of, or between approximately any two of, the following: 0.5, 0.75, 1.0, 1.25, and 1.5 cm. Each of perforations 62 of sorbent layer 54 may comprise a size (e.g., as measured by a maximum transverse dimension of the perforation) that is substantially smaller than the size of one or more of openings 66, such as, for example, 50, 60, 70, 80, or 90 percent smaller in size.

Figure 4:
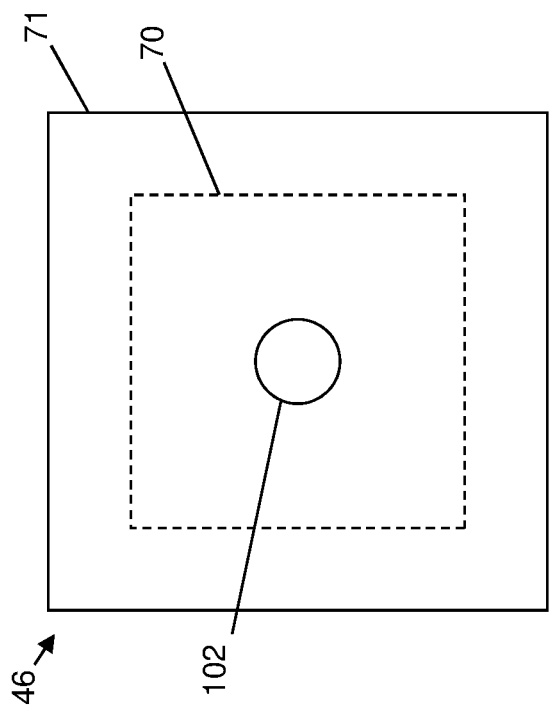
FIG. 4 is a top view of an embodiment of a manifold, suitable for use in some embodiments of the present systems.

Sorbent layer 54 can comprise any suitable planform shape, planform area, thickness, and/or the like appropriate to treat target tissue 22. As shown in FIG. 4, a planform area of sorbent layer 54 (depicted by dotted line 70) is smaller than a planform area of manifold 46 (depicted by solid line 71) such that, when sorbent layer 54 is disposed between manifolds 46 (i.e., when a manifold is disposed on opposing sides of the sorbent layer), the opposing manifolds can be coupled around a peripheral edge of the sorbent layer to define a pocket. For example, the planform area of sorbent layer 54 is at least 10 percent smaller, such as, for example, 15, 20, 25, 30, 35, 40, or 45 percent smaller than the planform area of manifold 46. In this way and others, therapeutic gas can circumvent sorbent layer 54 and be distributed from a manifold 46 on a first side of the sorbent layer to a manifold 46 on an opposing second side of the sorbent layer.

Dressing 18 can include a gas-occlusive layer 74. Gas-occlusive layer 74 can be configured to be disposed over one or more manifolds 46 and coupled to tissue 30 surrounding target tissue 22 such that an interior volume 78 is defined between the gas-occlusive layer and the target tissue and such that the gas-occlusive layer limits escape of therapeutic gas and/or exudate from the interior volume between the gas-occlusive layer and the tissue surrounding the target tissue. A portion of gas-occlusive layer 74 can be coupled to tissue 30 surrounding target tissue 22 via patient-interface layer 26. To illustrate, a tissue-facing surface of gas-occlusive layer 74 can comprise an adhesive, such as, for example, an acrylic adhesive, polyurethane gel adhesive, silicone adhesive, a combination thereof, and/or the like, configured to couple the gas-occlusive layer to patient-interface layer 26 and/or tissue 30 surrounding target tissue 22. For example, when gas-occlusive layer 74 is coupled to patient-interface layer 26, such an adhesive may flow through one or more of openings 38 of the patient-interface layer to adhere gas-occlusive layer 74 to tissue 30 surrounding target tissue 22.

Gas-occlusive layer 74 can comprise a first opening 98 configured to allow communication of therapeutic gas into interior volume 78 of dressing 18. For example, first opening 98 of gas-occlusive layer 74 can be configured to receive a port (e.g., 94).

In this embodiment, dressing 18 comprises a filter 110 configured to filter fluid that flows through first opening 98 of gas-occlusive layer 74. For example, filter 110 can be sterile such that the filter provides a viral and/or bacterial barrier. As shown in FIGS. 2, 6A, and 6B, filter 110 comprises a layer of material that is bonded to a lower (e.g., tissue-facing) surface of gas-occlusive layer 74. In some embodiments, a filter (e.g., 110) comprises a layer of material that is bonded to an upper surface of a gas-occlusive layer (e.g., 74). Filter 110 can comprise any suitable material, such as, for example, polytetrafluoroethylene (PTFE) (e.g., an expanded PTFE), polyolefin, and/or the like. Filter 110 can comprise a backing material, such as, for example, a non-woven textile. Filter 110 may comprise a hydrophobic material. To illustrate, filter 110 can be configured to allow communication of therapeutic gas into interior volume 78 through first opening 98 of gas-occlusive layer and restrict communication of exudate out of the interior volume through the first opening of the gas-occlusive layer. Filter 110 can comprise a pore size of approximately 0.05 to 0.15 micrometers (e.g., approximately any one of or between any two of the following: 0.05, 0.07, 0.09, 0.10, 0.11, 0.13, and 0.15 micrometers).

A non-limiting example of filter 110 includes GORE® Microfiltration Media for Medical Devices, which is commercially available from W. L. Gore & Associates, Inc., of Newark, Del., USA.

Dressing 18 can comprise one or more second openings 99 configured to allow communication of therapeutic gas out of interior volume 78 of dressing 18. In this embodiment, gas-occlusive layer 74 comprises one or more second openings 99.

As shown in FIGS. 5A and 5B, second openings 99 can be arranged to encourage an even distribution of therapeutic gas flow out of interior volume 78 through each second opening. For example, as shown in FIG. 5A, one or more of second openings 99 may be arranged such that the second opening at does not overly one or more manifolds 46 and/or sorbent layer 54 (depicted by phantom line 100). For further example, as shown in FIG. 5B, one or more of second openings 99 may be arranged such that the second opening at least partially overlies one or more manifolds 46 and/or sorbent layer 54 (depicted by phantom line 100). As shown, for each second opening 99, a distance 101 (e.g., the shortest distance) between the second opening and first opening 98 of gas-occlusive layer 74 is approximately equal to a distance (e.g., the shortest distance) between each other of the second openings and the first opening.

Dressing 18 can be configured to cause a positive pressure to be attained and controlled within interior volume 78 when therapeutic gas source 14 supplies therapeutic gas to the interior volume. As used herein, "positive pressure" can refer to a pressure that is greater than a local ambient pressure, such as greater than atmospheric pressure. For example, positive pressure within interior volume 78 can be any suitable pressure (e.g., approximately any one of, or between approximately any two of the following: 5, 10, 15, 20, 25, 30, 35, and 40 mmHg) that encourages therapeutic gas to flow toward target tissue 22 and does not cause separation between dressing 18 and tissue 30 surrounding the target tissue.

Positive pressure within interior volume 78 can be attained in one or more ways. For example, to attain a positive pressure within interior volume 78, at least one second opening 99 can be sized to allow therapeutic gas to flow out of interior volume 78 through the at least one second opening at a volumetric flow rate that is at least 5 percent (e.g., 5, 10, 15, 20, or 25 percent or more) less than a volumetric flow rate at which first opening 98 and/or filter 110 allow therapeutic gas to flow into the interior volume. More particularly, first opening 98 can comprise a first size (e.g., as measured by a maximum transverse dimension of the first opening) and at least one second opening 99 can comprise a second size (e.g., as measured by a maximum transverse dimension of the second opening) that is at least 20 percent (e.g., 20, 25, 30, 35, 40, 45, 50, 55, 60, 65, 70, 75, 80, 85, 90, or 95 percent) smaller than the first size. For example, one or more second openings 99 can include a transverse dimension of approximately 1 to 10 millimeters (mm) (e.g., approximately any one of, or between approximately any two of the following: 1, 2, 3, 4, 5, 6, 7, 8, 9, or 10 mm). One or more second openings 99 can be sized to control the duration of time needed to reach a steady-state oxygen concentration of at least 80 percent within dressing 18. To illustrate, for the same volumetric flow rate of therapeutic gas, increasing the transverse dimension of one or more second openings 99 may cause the duration of time needed to reach a steady-state oxygen concentration of at least 80 percent to increase, and vice versa.

Dressing 18 can comprise one or more filters 110a, each of which are substantially similar to filter 110 with the exception that each filter 110a can be configured to allow communication of therapeutic gas out of interior volume 78 through second openings 99. Like filter 110, each filter 110a can be configured to restrict communication of exudate out of the interior volume through a respective second opening 99.

One or more filters 110a can be arranged such that a respective second opening 99 overlies at least a portion of the filter. For example, like filter 110, one or more filters 110a can comprise a layer of material that is bonded to an upper or lower surface of gas-occlusive layer 74. In some embodiments, one or more filters (e.g., 110a) can comprise a layer of material that is bonded to an upper or lower surface of a manifold (e.g., 46).

To attain a positive pressure within interior volume 78, at least one filter 110a can comprise a porosity configured to allow therapeutic gas to flow out of interior volume 78 at a volumetric flow rate that is less than a volumetric flow rate at which first opening 98 and/or filter 110 allow therapeutic gas to flow into the interior volume. More particularly, one or more filters 110a can comprise a porosity such that a volumetric flow rate of therapeutic gas out of interior volume 78 through the one or more filters 110a is at least 5 percent (e.g., 5, 10, 15, 20, 25 percent or more) less than a volumetric flow rate at which first opening 98 and/or filter 110 allow therapeutic gas into the interior volume.

As shown in FIG. 5C, dressing 18 may comprise a relief conduit 103 in fluid communication with interior volume 78 and configured to allow communication of therapeutic gas out of the interior volume. For example, relief conduit 103 can be disposed between patient interface layer 26 and tissue 30 surrounding target tissue 22. In some embodiments, a relief conduit (e.g., 103) can be disposed between any two of the following components of a dressing (e.g., 18): a manifold (e.g., 46), a patient interface layer (e.g., 26), a gas-occlusive layer (e.g., 74), and a sorbent layer (e.g., 54). Relief conduit 103 can be sterile such that the conduit provides a viral and/or bacterial barrier.

To attain a positive pressure within interior volume 78, relief conduit 103 can be sized to allow therapeutic gas to flow out of interior volume 78 through the relief conduit at a flow rate that is at least 5 percent (e.g., 5, 10, 15, 20, 25 percent or more) less than a flow rate at which first opening 98 and/or filter 110 allow therapeutic gas to flow into the interior volume.

Gas-occlusive layer 74 can be sterile such that the gas-occlusive layer provides a viral and/or bacterial barrier to target tissue 22. Gas-occlusive layer 74 can be configured to provide a layer of protection from physical trauma to target tissue 22. In some embodiments, a portion of a gas-occlusive layer (e.g., 74) may be configured to be gas-permeable to provide a suitable (e.g., moist) wound healing environment and/or to prevent passive permeation of therapeutic gas molecules through the gas-occlusive layer. Gas-occlusive layer 74 can comprise an oxygen permeability coefficient $(P \times 10^{10})$, at 25 degrees Celsius, ranging from 0.0003 and 0.5 (e.g., approximately any one of, or between approximately any two of the following: 0.0003, 0.0004, 0.0005, 0.0006, 0.0007, 0.0008, 0.0009, 0.001, 0.005, 0.01, 0.05, 0.1, 0.15, 0.2, 0.25, 0.3, 0.35, 0.4, 0.45, and 0.5), where P is measured in units of $[(cm^3)(cm)]/[(cm^2)(s)(cm\ Hg)]$ which represents [(amount of permeate)(gas-occlusive layer thickness)]/[(surface area)(time)(pressure-drop across the gas-occlusive layer)]. Gas-occlusive layer 74 can comprise a moisture vapor transmission rate (MVTR) of at least 250 grams per meters squared per day $(g/m^2/day)$. In embodiments where a tissue-facing surface of gas-occlusive layer 74 comprises an adhesive (as discussed above), the adhesive may affect the gas permeability and/or the MVTR of the gas-occlusive layer. To illustrate, for a gas-occlusive layer (e.g., 74) having a film with a thickness of 0.025 mm and an adhesive with a thickness of 0.025 mm, the gas permeability and MVTR of the gas-occlusive layer are 50 percent of a gas permeability and MVTR of a gas-occlusive layer (e.g., 74) without the adhesive.

Gas-occlusive layer 74 may comprise a flexible film, such as, for example, a hydrocolloid sheet. Gas-occlusive layer 74 can comprise any suitable material that limits escape of therapeutic gas and/or exudate through the gas-occlusive layer, such as, for example, polyurethane, polyethylene, polyvinyl acetate, polyvinyl chloride, polyvinylidene chloride, isobutylene, a halogenated isomer, a copolymer thereof, or a blend thereof. Gas-occlusive layer 74 can comprise any suitable planform shape, planform area, thickness, and/or the like that is appropriate to treat target tissue 22. For example, gas-occlusive layer 74 can comprise a thickness that is approximately any one of, or between approximately any two of the following: 10, 15, 20, 25, 30, 35, 40, 45, 50, 55, and 60 micrometers.

Dressing 18 can comprise a valve 82 coupled to gas-occlusive layer 74. Valve 82 can be configured to permit communication of gas out of interior volume 78 through the valve and prevent communication of gas into the interior volume through the valve. For example, valve 82 can be configured to relieve pressure within interior volume 78 when the pressure within the interior volume exceeds a threshold pressure. Such a threshold pressure may range from 8 to 24 mmHg (e.g., approximately any one of, or between approximately any two of the following: 8, 10, 12, 14, 16, 18, 20, 22, and 24 mmHg). Valve 82 can comprise any suitable one-way valve, such as, for example, a ballcheck valve, a thin film valve, a diaphragm check valve, and/or the like. In this way and others, valve 82 can be configured to ensure that interior volume 78 does not become over-pressurized with therapeutic gas such that dressing 18 and tissue 30 surrounding target tissue 22 separate to allow therapeutic gas therebetween.

Gas-occlusive layer 74 may comprise an oxygen sensor 86 configured to collect data indicative of the presence, volume, and/or concentration of oxygen within interior volume 78. Oxygen sensor 86 may comprise a display 90 configured to indicate, such as, for example, via a color change, the presence, volume, and/or concentration of oxygen within interior volume 78.

Dressing 18 may comprise a port 94 configured to be coupled to first opening 98 of gas-occlusive layer 74. Port 94 comprises one or more latching and/or interlocking features such that the port can be releasably coupled to therapeutic gas source 14 and/or valve 24 via conduit 19. For example, port 94 can be configured to be releasably coupled to therapeutic gas source 14 such that the therapeutic gas source can be decoupled from the port without removing dressing 18 from target tissue 22 and/or tissue 30 surrounding the target tissue.

Port 94 can be configured to allow fluid communication of therapeutic gas from therapeutic gas source 14 to interior volume 78 of dressing. A non-limiting example of port 94 includes the SensaT.R.A.C.™ Pad, which is commercially available from Kinetic Concepts Inc., of San Antonio, Tex., USA.

As shown in FIGS. 6A and 6B, dressing 18 can be configured such that port 94 can extend through one or more components (e.g., 46, 54, and/or 74) of the dressing to guide therapeutic gas toward target tissue 22, promote distribution of therapeutic gas within interior volume 78, and/or encourage removal of therapeutic gas having an oxygen concentration that is less than the oxygen concentration within the therapeutic gas when it enters the interior volume. In this way and others, dressing 18 can be configured to rely less on manifold(s) 46 and/or sorbent layer 54 to guide therapeutic gas toward target tissue 22, distribute therapeutic gas within interior volume 78, and/or encourage removal of therapeutic gas from the interior volume.

For example, port 94 can be configured to extend through first opening 98 of gas-occlusive layer 74. Manifold 46 can include an opening 102 positioned relative to the edges of the manifold such that at least a portion of first opening 98 of gas-occlusive layer 74 overlies at least a portion of the opening of the manifold. For example, when port 94 is received by first opening 98 of gas-occlusive layer 74, the port can overly at least a portion of opening 102 of manifold 46. Port 94 can be configured to extend through both first opening 98 of gas-occlusive layer 74 and through opening 102 of one or more manifolds 46 to guide therapeutic gas toward target tissue 22, distribute therapeutic gas within interior volume 78, and/or encourage removal of therapeutic gas from the interior volume. More particularly, as shown in FIG. 6A, port 94 can extend through an upper manifold 46, sorbent layer 54, and a lower manifold 46. As shown in FIG. 6B, port 94 can extend through an upper manifold 46, sorbent layer 54, but not a lower manifold 46 (i.e., a manifold 46 disposed between sorbent layer 54 and target tissue 22). Such a lower manifold 46, as shown in FIG. 6B, can be configured to distribute therapeutic gas from port 94 across the lower manifold.

As shown in FIGS. 3, 6A, and 6B, sorbent layer 54 can include an opening 106 positioned relative to the edges of the sorbent layer such that at least a portion of first opening 98 of gas-occlusive layer 74 overlies at least a portion of the opening of the sorbent layer. For example, when port 94 is received by first opening 98 of gas-occlusive layer 74 and/or by opening 102 of one or more manifolds 46, the port can overly at least a portion of opening 106 of sorbent layer 54. Port 94 can be configured to extend through first opening 98 of gas-occlusive layer 74, through opening 102 of one or more manifolds 46, and opening 106 of sorbent layer 54 to guide therapeutic gas toward target tissue 22, distribute therapeutic gas within interior volume 78, and/or encourage removal of therapeutic gas from the interior volume.

Figure 7:
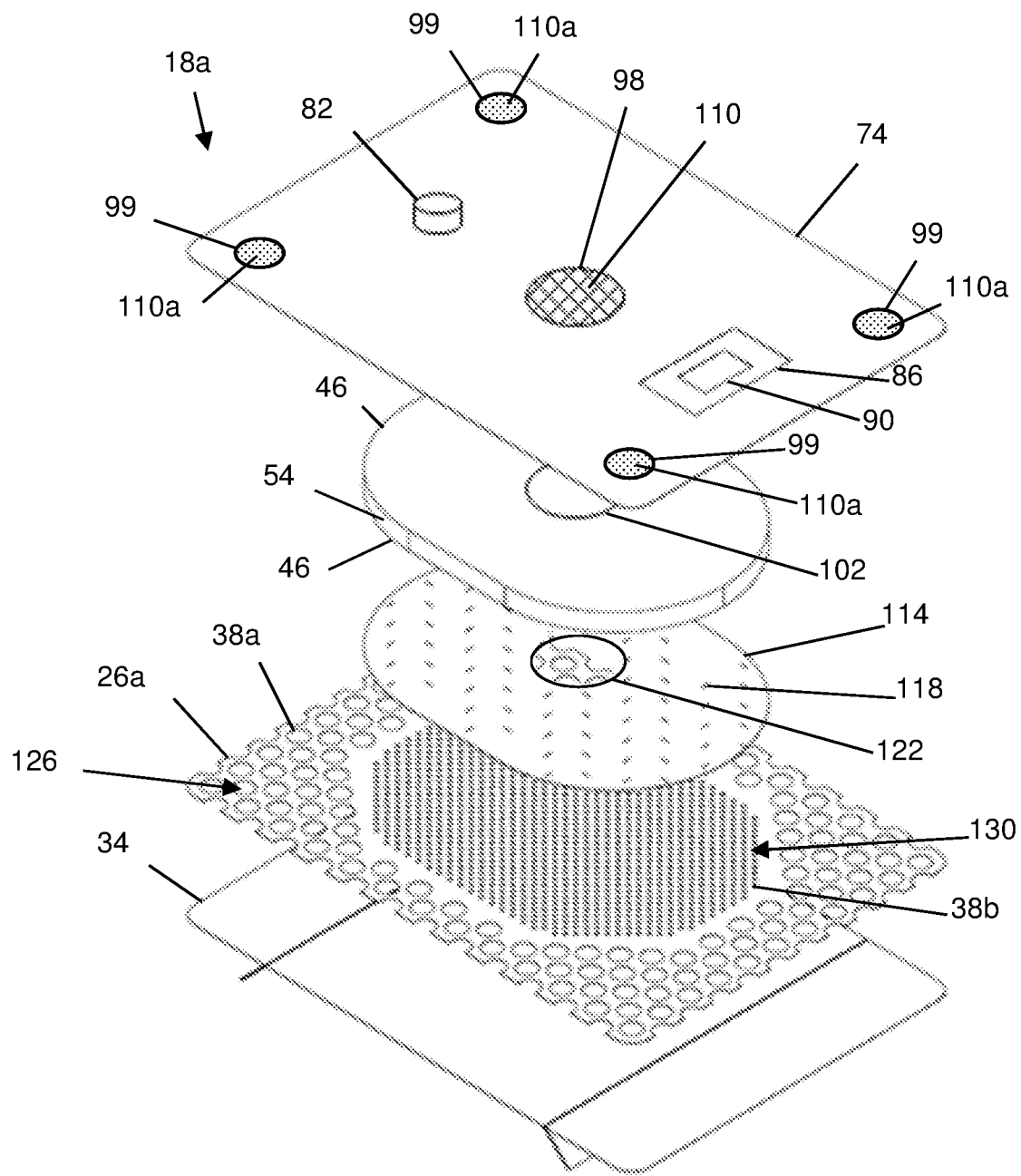
FIG. 7 is an exploded perspective view of a second embodiment of the present wound dressings, suitable for use in some embodiments of the present systems.

Referring now to FIG. 7, shown therein and designated by the reference numeral 18a is another embodiment of the present wound dressings for facilitating the delivery of therapeutic gas to target tissue 22. Dressing 18a is substantially similar to dressing 18, with the primary exception that dressing 18a comprises a liquid control layer 114 configured to be disposed between manifold 46 and target tissue 22 to restrict communication of exudate toward the target tissue. In some embodiments, a liquid control layer (e.g., 114) can be disposed between a manifold (e.g., 46) and a sorbent layer (e.g., 54).

Liquid control layer 114 can comprise a plurality of perforations 118 configured to permit exudate to flow away from target tissue 22 through the plurality of perforations and block the flow of exudate toward the target tissue through the plurality of perforations. Each perforation 118 may define an aperture comprising a perimeter that changes (e.g., changes by more than 5%) in response to fluid flow through the perforation. Each of perforations 118 of liquid control layer 114 may be substantially equal in size (e.g., as measured by a maximum transverse dimension of the opening), such as, for example, approximately any one of, or between approximately any two of, the following: 1, 2, 3, 4, or 5 millimeters (mm). For example, one or more of plurality of perforations 118 may comprise a slit.

Liquid control layer 114 can comprise any suitable material to restrict communication of exudate toward target tissue 22. For example, liquid control layer 114 can comprise a foam, a non-woven textile, and/or a film. For further example, liquid control layer 114 can comprise a hydrophilic material, such as, for example, a superabsorbent polymer.

Like manifold 46 and sorbent layer 54, liquid control layer 114 can include an opening 122 positioned relative to the edges of the liquid control layer such that at least a portion of first opening 98 of gas-occlusive layer 74 overlies at least a portion of the opening of the liquid control layer. For example, when port 94 is received by first opening 98 of gas-occlusive layer 74, by opening 102 of manifold 46, and/or by opening 106 of sorbent layer 54, the port can overly at least a portion of opening 122 of liquid control layer 114. Port 94 can be configured to extend through opening 122 of liquid control layer 114 to guide therapeutic gas toward target tissue 22, distribute therapeutic gas within interior volume 78, and/or encourage removal of therapeutic gas from the interior volume.

Dressing 18a includes a patient-interface layer 26a, which is substantially similar to patient-interface layer 26 with the exception that patient-interface layer 26a comprises a first portion 126 comprising a first plurality openings 38a having a first size (e.g., as measured by a maximum transverse dimension of the first opening), and a second portion 130 comprising a second plurality of openings 38b having a second size (e.g., as measured by a maximum transverse dimension of the second opening) that is at least 50 percent (e.g., 50, 55, 60, 65, 70, 75, 80, 85, 90, or 95 percent) smaller than the first size. In this embodiment, respective ones of second plurality of openings 38b of patient-interface layer 26a and respective ones of plurality of perforations 118 of liquid control layer 114 may be misaligned relative to each other to define a tortuous path for exudate flowing toward target tissue 22, thereby frustrating back flow of the exudate toward the target tissue. As shown in FIG. 7, patient-interface layer 26a can be configured to be disposed below liquid control layer 114.

Some of the present methods comprise coupling a wound dressing (e.g., 18, 18a) to a patient's tissue (e.g., 22, 30) and communicating therapeutic gas from a therapeutic gas source (e.g., 14) into the interior volume (e.g., 78) of the dressing, wherein the therapeutic gas is communicated at a flow rate of at least approximately 100 cubic centimeters per minute.

In some embodiments of the present methods, the flow rate at which the therapeutic gas is communicated into the interior volume is at least approximately 500 cubic centimeters per minute. In some embodiments of the present methods, the flow rate at which the therapeutic gas is communicated into the interior volume is approximately two liters per minute.

In some embodiments of the present methods, the therapeutic gas includes oxygen. In some embodiments of the present methods, the oxygen has an oxygen concentration of at least 90 percent.

Some embodiments of the present methods comprise communicating therapeutic gas from the therapeutic gas source to a negative pressure source (e.g., 23). In some embodiments of the present methods, when communicating the therapeutic gas between the therapeutic gas source and the negative pressure source, communication of the therapeutic gas between the therapeutic gas source and the interior volume of the dressing is restricted. In some embodiments of the present methods, the communication of the therapeutic gas between the therapeutic gas source and the negative pressure source is performed for a time duration of approximately five to seven seconds. In some embodiments of the present methods, after the time duration, the method includes communicating the therapeutic gas between the therapeutic gas source and the interior volume of the dressing. In some embodiments of the present methods, after the time duration, when communicating the therapeutic gas between the therapeutic gas source and the interior volume of the dressing, communication of the therapeutic gas between the therapeutic gas source and the negative pressure source is restricted. In some embodiments of the present methods, communication of the therapeutic gas from the therapeutic gas source is alternated between the negative pressure source and the interior volume of the dressing once approximately every 10 seconds.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A dressing configured to be coupled to tissue to facilitate delivery of therapeutic gas to the tissue, the dressing comprising:
   a manifold that defines a plurality of gas passageways, the manifold configured to allow communication of therapeutic gas to the tissue; and
   a gas-occlusive layer configured to be disposed over the manifold and coupled to the tissue such that an interior volume containing the manifold is defined between the gas-occlusive layer and the tissue and the gas-occlusive layer limits escape of therapeutic gas from the interior volume;
   wherein the gas-occlusive layer includes:
      a first opening configured to allow communication of therapeutic gas into the interior volume; and
      a plurality of second openings configured to allow communication of therapeutic gas out of the interior volume to an ambient environment, each of the plurality of second openings being spaced a uniform distance from the first opening.

2. The dressing of claim 1, wherein each of the plurality of second openings includes a transverse dimension of approximately 1 to 10 millimeters (mm).

3. The dressing of claim 1, wherein the gas-occlusive layer comprises a plurality of filters configured to allow communication of therapeutic gas out of the interior volume through the plurality of second openings and restrict communication of exudate out of the interior volume through the plurality of second openings.

4. The dressing of claim 3, wherein at least one of the one or more filters includes a pore size of approximately 0.05 to 0.15 micrometers.

5. The dressing of claim 3, wherein at least one of the one or more filters includes polytetrafluoroethylene or polyolefin.

6. The dressing of claim 1, comprising a liquid control layer having a plurality of perforations, the liquid control layer configured to be disposed between the manifold and the tissue to restrict communication of exudate toward the tissue.

7. The dressing of claim 6, wherein the liquid control layer includes an opening and at least a portion of the first opening of the gas-occlusive layer overlies at least a portion of the opening of the liquid control layer.

8. The dressing of claim 1, wherein the manifold includes an opening and at least a portion of the first opening of the gas-occlusive layer overlies at least a portion of the opening of the manifold.

9. The dressing of claim 1, comprising a port configured to extend through the first opening of the gas-occlusive layer to guide the communication of therapeutic gas into the interior volume.

10. The dressing of claim 9, wherein: the manifold includes an opening and at least a portion of the first opening of the gas-occlusive layer overlies at least a portion of the opening of the manifold; and the port is configured to extend through the opening of the manifold and an opening of a liquid control layer to guide the communication of therapeutic gas into the interior volume.

11. The dressing of claim 1, comprising a patient-interface layer configured to be disposed below the manifold and in contact with the tissue, the patient-interface layer defining a plurality of openings configured to allow communication of therapeutic gas and exudate through the patient-interface layer.

12. The dressing of claim 1, comprising a sorbent layer having a sorbent material configured to be disposed above or below the manifold and to capture exudate.

* * * * *